United States Patent [19]

Nuwayser

[11] Patent Number: 4,687,481
[45] Date of Patent: Aug. 18, 1987

[54] TRANSDERMAL DRUG DELIVERY SYSTEM

[75] Inventor: Elie S. Nuwayser, Wellesley, Mass.

[73] Assignee: BIOTEK, Inc., Woburn, Mass.

[21] Appl. No.: 835,154

[22] Filed: Mar. 3, 1986

Related U.S. Application Data

[62] Division of Ser. No. 653,362, Oct. 1, 1984, Pat. No. 4,624,665.

[51] Int. Cl.⁴ .............................................. A61M 7/00
[52] U.S. Cl. .................................... 604/897; 424/449
[58] Field of Search .................. 604/897, 896; 424/28

[56] References Cited

U.S. PATENT DOCUMENTS

| | | | |
|---|---|---|---|
| 2,561,071 | 7/1951 | Prisk | 604/897 |
| 3,964,482 | 6/1976 | Gerstel | 604/896 |
| 3,996,934 | 12/1976 | Ziffasoni | 604/897 |
| 4,291,015 | 9/1980 | Keith | 604/896 |
| 4,568,559 | 2/1986 | Nuwayser | 427/3 |
| 4,592,753 | 5/1986 | Panoy | 604/897 |

FOREIGN PATENT DOCUMENTS

| | | | |
|---|---|---|---|
| 0138120 | 10/1979 | Japan | 604/897 |
| 0002909 | 1/1981 | Japan | 604/897 |

*Primary Examiner*—Sam Silverberg
*Attorney, Agent, or Firm*—Richard P. Crowley

[57] ABSTRACT

A transdermal drug delivery system useful for the controlled, for example zero order release of one or more drugs to a selected skin area of a user, which system comprises an impervious backing sheet and a face membrane, the backing sheet and membrane secured together to form an intermediate reservoir. The face membrane is a macroporous membrane which has pores of sufficient size to avoid any rate control of the drug to be transdermally delivered to the user. The reservoir contains a viscous liquid base material selected to exude from the membrane to form a film and to occlude the skin of the user to force hydration of the stratum corneum with water from the lower layers of the epidermis of the user and a plurality of solid microparticles generally uniformly dispersed and suspended in the liquid base material. The microparticles containing an effective therapeutic amount of the drug for transdermal delivery, such as the contraceptive steroid. In use the liquid base material exuded from the macroporous membrane face forms a thermodynamically stable thin film layer in an intimate contact with the skin, while the drug is released from the microparticles into the base material and transdermally into the user.

18 Claims, 4 Drawing Figures

FIG. 3a IN VITRO

FIG. 3b IN RABBITS

TRANSDERMAL DRUG DELIVERY SYSTEM

REFERENCE TO PRIOR APPLICATIONS

This is a divisional of co-pending application Ser. No. 653,362, filed on Oct. 1, 1984, now U.S. Pat. No. 4,624,665.

This application discloses to a prior co-pending application U.S. Ser. No. 577,079, filed Feb. 6, 1984, entitled COMPOSITE CORE COATED MICROPARTICLES AND PROCESS OF PREPARING SAME now U.S. Pat. No. 4,568,559, issued Feb. 4, 1986. The prior application relates to a process for preparing coated solid microparticles and to the microparticles so prepared and to the use of the microparticles to provide for the sustained release of a drug incorporated in the microparticles. The process comprises preparing a solvent solution of an active ingredient such as a drug to be encapsulated, but more particularly a contraceptive steroid-type drug and a film-forming polymer and removing the solvent to provide a dry, composite, uniform admixture of the drug-active ingredient and the polymer material. The mixture is then reduced to a defined, smaller particle size distribution and the ground admixture then coated in a fluidized bed with a uniform, defined wall thickness of the same or substantially the same film-forming polymer material used to provide the composite core coated microparticles. Typically, the dry composite admixture is reduced to a particle size of less than 1000 microns, e.g. 200 microns. The film forming polymer material employed generally is a polymer, like polyvinyl alcohol or a cellulosic material or a biodegradable polymer, such as for example, a polyactide, a polyglycolide, and copolymers of lactides and glycolides. The drug employed in the microparticles may vary, but typically may comprise for example, a contraceptive steroid-type drug such as levonorgestrel or estradiol. For injectable compositions the particle size of the microparticles is less than 200 microns with a uniform wall coating of about 0.2 to 20 microns. The microparticles are useful for the controlled release of a drug-active ingredient such as in a zero order release pattern and for example, may be employed by injecting microparticles suspended in a liquid carrier into a patient.

BACKGROUND OF THE INVENTION

Transdermal delivery of medication is not a new concept, as a variety of medications that are readily available for delivery through the skin have been available in ointment form for over thirty years. With ointments, however, it is difficult to achieve precise drug dosage. In a transdermal patch system, this problem is eliminated by controlling the rate of drug release over a prescribed perior of time. Patches are worn behind the ear, on the chest, or on the arm and dispense a drug for as long as a week at a time. For certain drugs transdermal delivery has significant advantages over oral administration. It eliminates "first pass" inactivation by the liver and irregular gastric absorption. Because of constant absorption through the skin, it maintains relatively constant blood levels of the drug.

Two drugs, scopolamine and nitroglycerin, have recently become commercially available in transdermal form. Although there are differences in composition and in the mechanism of drug delivery among the available transdermal delivery systems, they all appear to be functionally similar. Generally the systems have essentially steady state reservoirs sandwiched between an impervious backing and a membrane face. The systems usually are attached to the skin by an adhesive gel. Some products have a rate-controlling outer microporous membrane. One product depends on a diffusion matrix in which nitroglycerin molecules are in equilibrium between lactose crystals and the liquid phase. In another product, micropockets of nitroglycerin are evenly dispersed throughout a silicone polymer which controls the drug release rate and prevents dose dumping.

A description of the different commercial products which deliver nitroglycerin transdermally is set forth by Dasta, et al., *American Pharmacy*, NS22, 2, 29–35, Feb. 1982, which article also illustrates the various prior art nitroglycerin patches and their construction and operation, and which article is hereby incorporated by reference.

U.S. Pat. No. 4,336,243, issued June 22, 1982 describes transdermal nitroglycerin pads wherein the pad comprise a silicone polymer matrix being a cross-linked silicone rubber having from about 10 to 200 microns microseal compartments formed by the in situ cross-linking of the silicone rubber after it is admixed with a hydrophilic solvent containing the nitroglycerin in a hydrophobic solvent which enhances the dispersion and transport. U.S. Pat. No. 4,053,580, issued Oct. 11, 1977 describes an earlier pharmaceutical delivery device employing a silicone polymer matrix wherein the rate of release of the active ingredient is controlled by altering the solubility of the hydrophilic solvent system for the polymer matrix.

Another polymer diffusion matrix transdermal delivery system is described in published European patent application 80300038.9, of A. Keith entitled Polymeric Diffusion Matrix and Method of Preparation and Drug Delivery Device Comprising Said Matrix. This application describes a polymeric diffusion matrix composed of glycerol and polyvinyl alcohol together with a water-soluble polymer to provide a polymer matrix capable of sustained release of a drug dispersed in the matrix. Typically, the water-soluble polymer comprises a polyvinylpyrrolidone or a water-soluble cellulosic derivative. U.S. Pat. No. 3,797,494, issued Mar. 19, 1974 describes a transdermal bandage which includes a reservoir with a drug confined within the interior chamber of the reservoir and distributed throughout a reservoir matrix. In one embodiment the drug is released by a controlling microporous material, which microporous material meters the flow of the drug into the skin at a controlled rate. In another embodiment an adhesive coating is uniformly distributed through microcapsules comprising a drug encapsulated with a microporous rate controlling material.

While many transdermal drug delivery systems have been described as an economical and effective transdermal drug delivery system particularly for the delivery of contraceptive steroid drugs is still needed, and desired, particularly percutaneous delivery of steroid contraceptives in a controlled manner for periods of time ranging from one to four weeks or more.

Levonorgestrel is a synthetic steroid which has powerful progestational activity with minimal side effects at very low doses. Estradiol is a natural estrogen which has limited oral effectiveness because of "first pass" inactivation during circulation. On the other hand the synthetic steroid, ethinylestradiol, is active orally, since its inactivation by the liver and other tissues is very low. These contraceptives and others like Mestranol, Norethindrone, etc., are employed in various oral contraceptives manufactured in this country. Although levonorgestrel pills contain 150 micrograms of the drug, studies with implantable drug delivery systems indicate that only 30 micrograms per day are sufficient to prevent fertility.

Thus, it is desirable to provide an effective transdermal drug delivery system for the transdermal delivery of drugs, particularly contraceptive steroids.

SUMMARY OF THE INVENTION

The invention concerns a transdermal drug delivery system and a method of manufacture and use of such system. In particular the invention relates to a transdermal drug delivery system particularly useful for the controlled release of a contraceptive steroid drug or a combination of such drugs.

The invention relates to a transdermal drug delivery system which may be employed with a drug which is desired to be delivered transdermally at a controlled or sustained rate, typically a zero order rate or other delivery release patterns as desired. The transdermal drug delivery system of the invention prevents dose dumping of the drug caused by accidental rupture of the retaining member and ensures effective and prolonged delivery of the drug.

The invention relates to a method of and system for accelerating the transdermal delivery of drugs into a patient by sealing the skin of the patient with a thin layer of a viscous material to occlude the skin and transporting a desired dosage of a drug across the thin layer typically from a rate-controlling system in contact with the thin layer. The rate-controlling system may be a thin rate-controlling membrane interposed between the drug and the thin layer. Preferably the rate-controlling system comprises microparticles of the drug or a combination of drugs to be delivered suspended in the same or similar viscous material and contained within a container system. The container system generally comprises a macroporous non-rate-controlling face membrane with an impervious backing to form a pool or patch-like system of desired face membrane area with the face of the membrane placed over and in contact with the thin occluding viscous layer on the skin. The thin viscous layer may be coated or placed on the skin repeatedly and the patch system placed on top of the thin viscous layer or the viscous layer formed in situ by exudation through the membrane face when the patch or pool system is placed in position on the skin. The patch or pool container system generally is retained in a transdermal position by the use of a peripheral adhesive layer about the patch or pool. Typically the face or transport area of the membrane is covered prior to use by a removable cover such as a peelable strip of impervious sheet material.

In another embodiment microcapsules containing a drug for delivery may be suspended in a viscous material and the composition then spread as a layer over the skin of the user with or without a covering material.

The present drug delivery system for the transdermal delivery of medicaments is based on the use of solid microparticles. The system releases the drug from rate-controlling microparticles which are suspended in a dermatologically acceptable viscous liquid base. Drug release from microcapsules is controlled by microcapsule size and wall thickness. The system is also characterized by a macroporous membrane which delivers a thin liquid film of the base vehicle to the skin and whose function is to deliver the drug to the skin. The function of the viscous liquid film is to occlude the skin causing the stratum corneum to swell and hydrate by forcing the diffusion of water from the lower layers of the epidermis and thus to accelerate the drug delivery. The first phase in transdermal delivery is dependent on the rate of diffusion of the drug within the vehicle and its rate of release from the vehicle. The drug concentration in the vehicle determines the thermodynamic activity and influences the diffusion of the drug out of the vehicle.

The present drug delivery system suspends drug/polymer microparticles, in a delivery vehicle which microparticles control the rate of release of the drug to the vehicle. Drug delivery from microcapsules is zero order provided solid particles are present inside the microcapsule in equilibrium with a saturated solution of the drug. It is dependent on the diffusion coefficient of the drug in the polymer, the thickness of the capsule wall, and the microcapsule dimensions in accordance with this equation:

$$\frac{dM_t}{dt} = 4\pi DK\Delta \frac{r_o r_i}{r_o - r_i}$$

Where M is the mass of the drug released, d/dt is the steady state release rate at time t, DK is the membrane permeability, D is the diffusion coefficient of the drug in the membrane in cm$^2$/sec., K is the distribution coefficient, C is the difference in drug concentration between the internal and external surface of the membrane, and $r_o r_i$ are the outer and inner radii of the capsule wall, respectively.

Drug release from monolithic microparticles such as microspheres is first order and is additionally dependent on drug concentration in the particle. Thus, the presence of the microparticles in the base vehicle helps to maintain a constant thermodynamic activity of the drug in the vehicle by insuring that the concentration of the drug is close to saturation.

The delivery of the vehicle to the skin is regulated by a macroporous membrane (for example ranging from about 1 to 1000 microns) whose properties and pore size are selected to match those of the base vehicle. A hydrophobic membrane, for example, is best used with a hydrophobic delivery base vehicle and membrane with a hydrophilic vehicle while smaller micron pores e.g. 50 to 200 deliver a smaller quantity of the vehicle than larger micron pores e.g. 300 to 600.

The principal barrier to permeation of small molecules through the skin is provided by the stratum corneum or "horny layer" of cells which is about 10 to 15 microns thick. This layer is composed of a dispersion of hydrophilic proteins in a continuous lipid matrix. The lipid component of the layer which comprise only 20–30% of the weight of the tissue are directly responsible for its unique low permeability (Scheuplein, 1971). The stratum corneum may be regarded as a passive diffusion membrane, albeit not entirely inert, which follows Fick's Law in which the steady state flux Js is:

$$Js = \frac{Km\ D\ Cs}{S}$$

where $$Km = \frac{\text{solute sorbed per cc of tissue}}{\text{solute in solution per cc solvent}} = \frac{Cn}{Cs}$$

Cs = concentration difference of solute across membrane

D = average membrane diffusion coefficient for solute

S = membrane thickness

Swelling of the corneum can be produced by hygroscopic or other substances if they penetrate the hydrophilic zone or if lipophilic substances penetrate the hydrophobic zones. Increasing the state of hydration increases the porosity and thickness of the layer and favorably influences the transport of the drug by two to three fold. The simplest method for increasing hydration is to occlude the skin which forces the diffusion of water from the lower layers of the epidermis. Estimated diffusion content constant for low molecular weight nonelectrolyte is $10^{-9}$ cm. sq./sec. for stratum corneum and $10^{-6}$ cm. sq./sec. for the dermis.

The degree of hydration of the stratum corneum is provided by the macroporous membrane which delivers a thin liquid film of the vehicle to its outer surface to occlude the skin. The liquid film is simultaneously in contact with the skin and the liquid or viscous vehicle of the reservoir through the macroporous channels of the membrane. Occlusion of the skin which follows may be influenced by the properties of the vehicle and the membrane.

Following topical administration of many drugs including steroids like estrogen and norgesterone, a reservoir can form in the skin. The existence of this reservoir and its localization in the stratum corneum was first proven by Vickers (1963). Much of the work in this area has dealt with local action of drugs (e.g. hexachlorophene, sunscreens, cortisol). However, prolonged toxic response following topical administration of vasoconstrictors demonstrates that a cutaneous reservoir can provide sustained release into the systemic circulation. Accumulation of both estrogen and progesterone in subcutaneous tissue and underlying muscle has been observed and is more pronounced with percutaneous than with subcutaneous administration. The duration of the local reservoir appears to be dependent on the normal 14 day cycle of epidermal turnover. Irritation with a detergent or methotrexate increases turnover and can reduce the duration of the reservoir by nearly 50%. Inhibition of turnover with fluorinated steroids can double the duration to 28 days. In addition a compound which very rapidly penetrates and diffuses is maintained in the reservoir for a short period of time (e.g. nicotine, 3-4 days). Since occlusion of the area of application appears necessary to promote sustained absorption from the reservoir, continued absorption following removal of the delivery system should be minimal unless the concentration is very high.

Pronounced and prolonged effects of estrogens and gestagens can be expected by the transdermal route since it is the total amount of hormone absorbed by the body that is decisive, and not the peak height of the hormone level. The flux rate of steroids through human skin has been studied by others and are shown below Table 1.

TABLE

| STEROID | FLUX RATES OF STEROIDS | |
|---|---|---|
| | FLUX (MOLES/CM$^2$ HR). (Feldman 1969) | (SCHAEFER 1979) |
| 17β estradiol | $8.2 \times 10^{-11}$ | $5.8 \times 10^{-10}$ |
| 17β estradiol | | $4.6 \times 10^{-10}$ |
| Testosterone | $5 \times 10^{-11}$ | $1 \times 10^{-9}$ |
| Estriol | | $7.8 \times 10^{-11}$ |
| Progesteone | $3.4 \times 10^{-11}$ | |
| Hydrocortisone | $2.5 \times 10^{-11}$ | |
| Corticosterone | $7.5 \times 10^{-12}$ | |

Table I shows that the flux rates of estrodiol and progesterone are fairly high in comparison to the corticosterones. These flux rates depend on the concentration of the applied substance in the vehicle. At low concentrations the rates are proportional to the concentration in the vehicle. This proportionality is not 1 to 1 since a doubling of the concentration increases the flux by about 30-50%.

This general pattern of regional variation was found to hold for other chemical moieties (steroids, pesticides, and antimicrobials). Although the stratum corneum is generally accepted to be the major barrier to percutaneous penetration, this appears to hold only if the skin is intact. Damage to the stratum corneum makes the other layers function as barriers. For example, the penetration of hydrocortisone through modified skin results in a tenfold increase in the penetration of hydrocortisone from 1% to 10% when the skin is occluded. The thin liquid film which is exuded by the macroporous membrane occludes the skin to increase drug penetration.

The drug delivery system of the invention is based on the use of drug polymer solid microparticles or rate-controlling microcapsules which are suspended in a dermatologically acceptable viscous liquid base material or vehicle. The base is separated from the skin by a non drug non rate-controlling macroporous membrane. The outer rim or perimeter of the membrane is covered by a nonsensitizing hypoallergenic adhesive layer or other means to secure the system to the skin which holds the microporous membrane in contact or adjacent to the skin and prevents loss of the drug to the surrounding area. The microcapsules release the drug to the base in a controlled release pattern and maintains it in a thermodynamically stable condition. Release is controlled by the selected microcapsule size and thickness of the microcapsule wall. Thus, controlled release is obtained and the presence of the microcapsules prevents dose dumping caused by accidental rupture of the retaining membrane and ensures a prolonged delivery of the drug.

An important feature of the drug delivery system in this embodiment is the macroporous retaining membrane which separates the liquid base from skin. This membrane delivers a thin film controlled amount of the base material to its outer face surface to contact the skin. The liquid film occludes the skin and forces hydration of the stratum corneum with water from the lower layers of the epidermis. This in turn accelerates delivery of the drug, e.g. steroids across the stratum corneum. Intimate contact between the skin and the thermodynamically stable viscous liquid base also ensures uniform delivery of the drug throughout the treatment period. Unlike microporous membranes, the macroporous membrane does not control the rate of drug delivery to the skin, but solely the amount and thickness of the film of liquid material in contact with the skin.

The macroporous membrane ensures the presence of a continuous drug-filled liquid base pathway between the viscous base reservoir and the skin. The dimensions of the macropores and the degree of hydrophobicity of the membrane are selected to match the properties of the liquid base (i.e. viscosity, hydrophobicity). The function of the macroporous membrane is to permit only a small, but sufficient quantity of the base material to pass through the pores to the skin surface without being messy or leaky.

Microparticles are suspended in the liquid base material to provide a thermodynamically stable base with a constant driving force of the drug in the liquid base. The microparticles or microspheres suspended in the liquid base material comprise solid mixtures of the drug in a polymer and one embodiment may comprise the microparticles as described in the assignee's co-pending application Ser. No. 577,079 (hereby incorporated by reference).

The transdermal drug delivery system of the invention usually includes an impervious backing sheet with a macroporous face membrane, the backing sheet and the macroporous membrane typically secured together generally along its edges to form an intermediate layer-like reservoir therebetween. The macroporous membrane has pores of sufficient size to avoid rate control of the active drug ingredient to be transdermally delivered, but of a the size sufficient to permit the liquid base material to be exuded therefrom so as to form a thin film of the base material for intimate contact with the skin of the user adjacent the face of the macroporous membrane.

The reservoir comprises a dermatologically-acceptable, generally viscous liquid base material, the viscosity should be sufficiently high to suspend the microparticles therein and to prevent leakage or excessive flow through the membrane pores, but low engough to permit the function of the thin film on the skin. A plurality of solid microparticles or microspheres are generally uniformly dispersed and suspended in the liquid base material within the reservoir. The microparticles include an effective therapeutic amount of an active drug ingredient or a combination thereof, such as a contraceptive steroid, like levonorgestrel or estradiol or a combination thereof for transdermal delivery for a particular therapeutic purpose such as contraception. The drug is present in an effective therapeutic amount within the microparticles suspended in the reservoir with the microparticles generally designed to provide for a zero order release of the active drug material. Preferably, the microparticles are composed of an admixture of a polymer with the active drug ingredient in the microparticles varying as desired, but generally from about 0.1 to 30 percent by weight, for example, 1 to 20 percent and wherein the microparticle has a thin polymer wall coating thereon such as a wall coating imparted in a fluid bed coating system or by other means. Typically an adhesive layer is placed about the periphery of the drug delivery system and usually an impermeable material such as a protective peel strip is secured to the open face of the macroporous membrane, which peel strip is to be removed just prior to use.

In use and on removing of the peel strip, the drug delivery system in the form of a patch is applied to the skin of the user at a desirable location and the patch adhered by an adhesive exposed after removal of the peel strip. The macroporous nature of the membrane permits the viscous liquid base material in the reservoir to exude through the macropores to form a thin film on the face of the macroporous membrane and places the macroporous membrane in intimate contact with the skin of the user thus forming a thin dynamically stable thin film. The active drug ingredient is released at a selected zero order rate from the plurality of microparticles suspended in the liquid material; and therefore, transported directly through the viscous liquid base material into the skin of the user. The drug delivery system of the invention contributes significantly to the accelerated permeation of the drug through the skin, since the skin is continuously in contact with the drug in solution. Further, since the skin is occluded to permit hydration of water from the lower layers, the permeation of the drug from the liquid base material into the hydrated stratum corneum is much faster than when a dry dehydrated corneum is presented. In addition, the skin is continuously in contact with the viscous liquid base material which is generally selected to have emollient properties. This emollient contributes to the accelerated delivery by maintaining the outer skin softness and pliability to assure continuous contact between the skin, the liquid base material and the membrane surface which is in quite a contrast to contact with a dry solid matrix of the prior art.

The drug polymer microparticles produce a thermodynamically stable liquid base as a source of the active drug and practically eliminates the problem of drug dose dumping if the membrane is accidentally ruptured as with prior art transdermal drug delivery systems. The rate of drug delivery may be modified and tailored by several variables, such as the microparticle size, composition, polymer composition, wall thickness, and the macroporous membrane properties and porosity and the selection of the viscous liquid base composition and properties as to the degree of hydrophilicity or hydrophobicity. The various additives may be compounded and added into the liquid base material, which compounds may be employed to impart special properties to the liquid base material; for example, to enhance diffusion, control steroid reservoir formation, improve antiseptic properties, reduce infection, control viscosity, or to add emollient or lubricant properties where prolonged usage of the transdermal drug delivery system is desired.

The liquid base material may comprise a variety of materials, but typically should be a viscous-type liquid material capable of suspending the plurality of solid microparticles therein and also to be exuded through the selected pores of the macroporous membrane so as to form a thin stable thermodynamic film on the skin of the user. The liquid base material should be dermatologically acceptable to the user. The viscosity of the liquid base material should be high enough so that the liquid base material will not run from the macropores of the macroporous membranes and deplete the reservoir or become messy to the user, and yet not high enough to prevent the liquid base material from entering the pores and forming the thin film on the skin of the user after a protective face layer has been peeled away from the outer face of the macroporous membrane. Typically, the liquid base material should have a gel or grease-like viscosity and properties.

The liquid base material should be selected to be compatible with and to permit the transport of the drug within the microparticles. Typically, if the drug is a low water soluble-type drug then the liquid base material would be a low water soluble base material generally matching the hydrophobicity of the drug and vice versa where the drug is water soluble, the liquid base material may be selected to be also water soluble so that there is transport and compatibility from the drug release through the wall of the microparticle and so the drug may move effectively through the liquid base material in the reservoir and onto the thin film adjacent the user directly into the skin of the user. For example, the liquid base material may comprise a hydrophobic material such as a long chain, e.g. $C_8$-$C_{22}$ hydrocarbon-type material particularly for use with water-insoluble or very low water soluble drugs, such as for example, a grease-like hydrocarbon such as a petroleum based jelly e.g. vaseline, a semisolid mixture of hydrocarbons having a mp of 38°–60° C. The liquid base material may comprise also a hydrophilic-type material such as a polyethylene glycol, glycerol, or a water solution placed in a gel-like form through the use of viscosity modifying additives or gel-like material such as polyvinylpyrrolidone, agar, proteins, thickeners and the like. In addition, it should be noted that the liquid base material in the reservoir may contain other modifying additives to impart other desirable properties, such as the use of emollients such as glycols like glycerine, viscosity controlling agents, preservatives, thickening agents, antibacterial agents, such as a quaternary ammonium compound, stabilizers, depletion indicating devices such as dyes, waxes and other material typically employed in pharmaceutical and cosmetic applications and which are dermatologically and pharmaceutically acceptable.

The macroporous membrane material comprises a sheet material having pores to permit the passage of the viscous liquid base material. The function of the membrane is merely to contain the viscous liquid within the reservoir and to permit a thin film to be formed on the face side of the membrane. The macroporous membrane may be formed of a variety of materials either synthetic or natural polymeric material, but typically a membrane material as used in the prior art, such as for example, of a cellulosic material, an ethylenevinyl acetate copolymer material, cellulose acetate material, vinyl halides, polyvinyl chloride, nylon, porous polyolefins such as polyethylene, polypropylene and fluorocarbons and other materials which are adapted to be formed with or have bores of controlled size.

The microparticles employed in the drug delivery system generally comprise solid microparticles wherein the core of the particle contains an admixture of a polymer together with one or more of the drugs which are to be delivered by the microparticles, the active ingredient in the core may comprise a, varying amount and range for example from 5 to 95 percent by weight, such as 20 to 80 percent by weight with the remainder made up a core polymer material. The amount of microparticles in the base material may vary and range from 5 to 70 percent, e.g. 10–30 percent by volume of the reservoir material. The microparticle comprises and has a wall thickness of generally the same or similar polymer as the core material. The core material, of course, may have other additives, such as binders, adhesives, fillers and the like. The microparticles may have a wall coating produced by coating of the solution in a fluidized bed to provide a generally uniform wall thickness.

The active drug ingredient may comprise a wide variety of materials or combinations and be selected for the particular therapeutic function desired to be transdermally released. Preferably, the active drug ingredient does not react with and is chemically inert with the liquid base material and with the synthetic film forming polymer material comprising the microparticle. The microparticle is generally less than 1000 microns and typically less than about 200 microns. The microparticles may comprising microspheres and the microparticles designed to deliver a constant and sustained dose of the active ingredient for periods ranging from several hours to several years; for example, one day to one month. In one embodiment the control erelease rate may be a zero order release rate. The microparticles may be formed of natural or synthetic polymeric materials both of the core material and the coating material and particularly with biodegradable polymers such as the lactides, glycolides, or copolymers of lactide and glycolide as biodegradable polymers. For example, in one embodiment microparticles may be prepared from employing an active drug steroid such as levonorgestrel or estradiol and combinations in admixture with a biodegradable (polylactide) polymer and then coated with a biodegradable (polylactide) polymer to prepare the microparticles.

The drug material to be used as the active ingredient may vary and comprise for example, antibiotics, antibacterial agents, hormones, steroids, or other therapeutic agents. However, the principles of the drug delivery system will be illustrated employing a contraceptive steroid hormone with a drug delivery system designed to provide for sustained release by transdermal delivery of a contraceptive hormone such as levonorgestrel or estradiol. The sustained release of the drug from the microcapsules should be such as for an effective amount to be transdermally delivered to the user in an amount to be effective for the purpose for which the drug is selected. For example, with contraceptive steroid hormones approximately 5 to 150 micrograms per day per user and generally 20 to 50 micrograms per day is sufficient to prevent female fertility when using a levonorgestrel drug as an active ingredient.

The drug delivery system may be in the form of a patch or bandage and wherein the face of the macroporous membrane in contact with the skin through the thin thermodynamically liquid layer may range as desired depended upon the transport mechanism and rate, but typically would range from about 1 to 30 square centimeters, and more typically 2 to 10 square centimeters.

The invention will be described for the purposes of illustration only in connection with certain embodiments; however, it is recognized that various changes, modifications, additions, and improvements may be made to the illustrated embodiments by a person skilled in the art all falling within the spirit and scope of the invention.

BRIEF DESCRIPTION OF THE DRAWING

FIGS. 3(*a* and *b*) is a graphical representation of the comparison of in vitro release and plasma levels of levonorgestrel from microcapsules.

DESCRIPTION OF THE EMBODIMENTS

Figure 1:
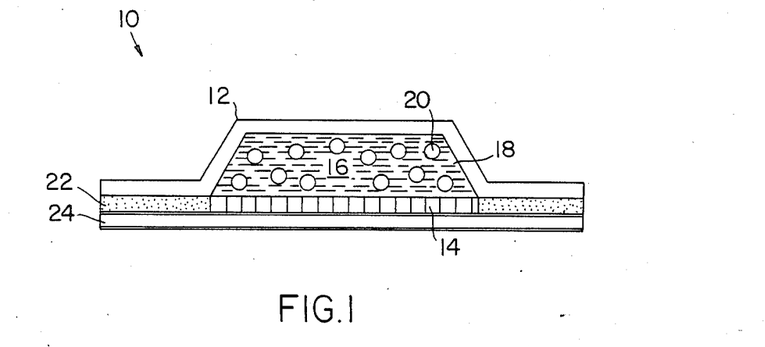
FIG. 1 is a schematic, sectional, illustrative view of the drug delivery patch system of the invention.
Figure 2:
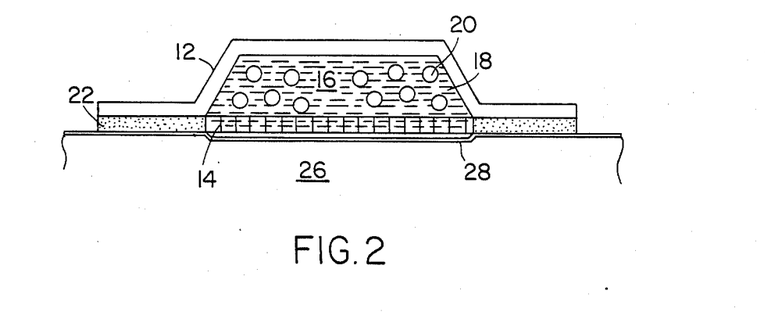
FIG. 2 is a schematic, sectional, and illustrative view of the patch delivery system of FIG. 1 as applied to the skin of a user.

FIGS. 1 and 2 show a bandage-type transdermal sustained release delivery system of the invention 10 wherein the device comprises an impervious backing sheet 12 and a macroporous face membrane 14 containing a plurality of macropores generally ,having a pore size of 200 to 500 microns and composed of an ethylene vinyl acetate copolymer. The backing sheet 12 and the macroporous membrane 14 form a generally flat reservoir 16 therebetween, the reservoir containing a viscous liquid base material 18 such as a viscous hydrocarbon vehicle like Vaseline. Uniformly suspended in the hydrocarbon of liquid viscous base there are a plurality of solid microparticles 20 containing, for example, levonorgestrel in an amount to deliver about 30 micrograms per day of the levonorgestrel from the microparticles in a zero order release over a period of one to four weeks. The microparticles 20; for example, those as prepared in the co-pending application generally comprise from about 5 to 75 percent by weight of the viscous liquid base material within the reservoir 16, e.g. 20 to 60 percent. Arround the peripheral edge of the backing material is an adhesive layer 22 while a removable peel strip 24 against the face of the macroporous membrane 14 prevents the discharge of the viscous liquid base material prior to use.

FIG. 2 shows the application of the bandage-type delivery system to the skin of a user 26 and illustrates that a thin liquid film 28 of the viscous liquid 18 in the reservoir 16 forms across the entire face of the macroporous membrane 14 to maintain intimate contact between the face of the macroporous membane 14 in the skin 26 and to accelerate the transdermal delivery of the drug from the microcapsules 20.

A typical sustained release for the release of levonorgestrel is: a 9.4 square centimeter of Johnson and Johnson Rayon™ First Aid Tape-Hypo-Allergenic—1 inch wide, 1.5 inch long for the impervious backing and to form the adhesive layer and a 2 square centimeter ID—2.25 square centimeter OD—$\frac{2}{3}$ mm thick teflon ring. The macroporous membrane may comprise 4.9 square centimeter Millipore Corp. F/LW 025 Fluoropore (PTFE) porous membrane—pore size 2.0 um, mean thickness 200 um, typical porosity 85 percent, hydrophobic material. Microspheres are prepared from the levonorgestrel and the poly-L(—)lactide as follows: Prepare a 2.5 percent wt/v solution of polyvinyl alcohol (PVA) #523 in one liter of distilled water; prepare a 15 percent wt/v solution of poly-L-(—)lactide, approx. 1 R.S.V. in 300 ml of reagent grade methylene chloride; mix 5 ml of the poly-L-(—)lactide solution, 10 ml methylene chloride and 5 grams of levonorgestrel to form a uniform slurry; take the 1 l of PVA solution and pour it into a 2 l stainless steel beaker. Stir at approx. 1000 RPM (1550×0.7) and heat at low temperature, (approx. 35° C.); add levonorgestrel slurry. Heat approx. 4 hours, then turn off heat and stirrer; wet sieve off the 45–106 um size fraction; and dry in vacuum oven at room temperature and recover the solid microspheres. Then 45 mg of these solid microspheres are mixed with 85 mg of Vaseline or a viscous vehicle (trademark of Chesebrough-Pond's, Inc.). The Teflon ring is placed in the center on the adhesive side of the tape and the Vaseline mixture is then spread to uniform thickness iside the Teflon ring. The porous membrane is then placed over the mixture of Vaseline to form a complete patch. An estradiol patch is similarly prepared using 70 mg of Vaseline with 38 mg of microspheres containing estradiol.

Figure 3A:
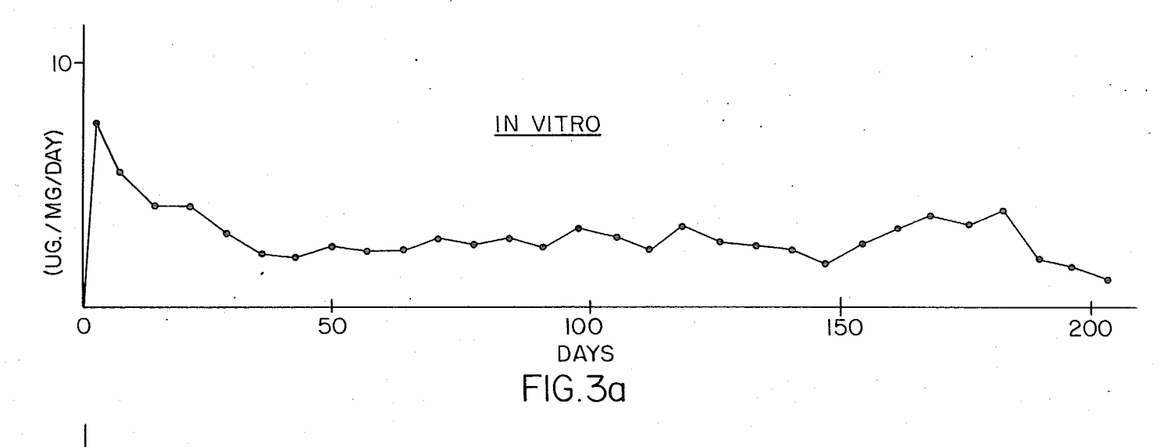

FIG. 3(a) illustrates an in vitro sustained release of levonorgestrel from a microparticle wherein the drug comprises about 10 percent of the microparticles and the biodegradable polymer of polylactide comprises about 90 percent by weight of the core material and wherein the wall thickness of the microparticle ranges from about 3 to 8 microns and is composed of the polylactide polymer.

Figure 3B:
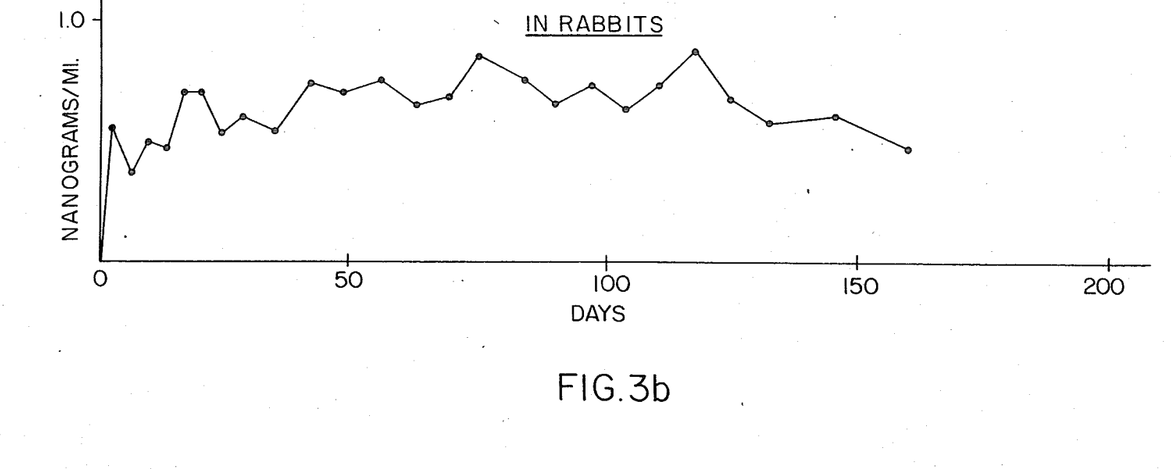

FIG. 3(b) illustrates the in vivo release of the hormone levonorgestrel into blood plasma of rabbits from the same microparticles as in FIG. 3(a). Thus, it is illustrated that the levonorgestrel microcapsules provide for a sustained generally zero order release of the contraceptive.

A transdermal delivery system known as DermaPatch has been developed which delivers levonorgestrel across freshly excised mouse skin at a dose of 43 micrograms/day from a 2.4 square centimeter patch. Drug release is sustained at a constant rate over a minimum period of 14 days. A system which delivers estradiol across freshly excised mouse skin at a dose of 5 micrograms/day from a 2.4 square centimeter patch has also been developed. A combined contraceptive system would constitute 20 micrograms/day of levonorgestrel, and 25 micrograms/day of estradiol over a period of 3–7 days which target doses can be delivered from a single 5–6 square centimeter patch system which contains both steroids.

In Vitro mouse skin permeation studies were conducted with a 2.4 square centimeter patch which was placed in a 20 mm diameter water jacketted Franz diffusion cell mounted on a 9-cell Drive Unit/Mounting Assembly. The water jacket temperature of the cells was controlled by a bath and water circulator which is maintained at 37° C. This system is widely used in the pharmaceutical industry for measuring the permeability of percutaneous patches across animal and cadaver skins. In the preliminary studies with levonorgestrel and estradiol it was discovered that the size of the cell reservoir was too small to permit overnight studies because the solution became saturated rapidly with the steroids within a few hours after startup so an adaptor was used for the Universal Diffusion Cell to permit overnight studies.

Release of each drug was determined as a function of time by analysis of aliquots of the contents of the reservoir in a Waters High Pressure Liquid Chromatograph (HPLC) using a u Bondpak C-18 radial pack column with a mobile phase of 60% ethanol in water. The steroids were measured in a uv detector at a wavelength of 280 nm for estradiol and 254 for levonorgestrel.

Pieces of full thickness abdominal skin were freshly excised from a 6 week old male nude mice and mounted individually on the Franz diffusion cell. Before use, the skins were washed three times in 200 ml normal saline to remove extraneous and other soluble material. The face membrane of the system was applied to the stratum corneum side of the skin. The skin permeation profile of each drug was followed by removing the liquid from the receptor compartment for assay at the appropriate intervals. The compartment was then filled with fresh saline and the permeation continued. Release of the drug was monitored in a liquid chromatograph (HPLC).

The results of the skin permeation studies indicated that levonorgestrel penetrates the abdominal skin of the nude mouse at a zero order rate. The rate of skin permeation for levonorgestrel delivered by the system during 24 hours is approximately 43 ug/day. The area of the membrane in contact with the skin was 2.4 square centimeters. This translates into a skin permeation rate of 1.8 ug/square centimeter/hour or 18 ug/square centimeter/day. This rate continued for a period of 14 days.

Table 2 summarizes the test data on levonorgestrel and estradiol mouse skin permeation tests:

TABLE 2

| LEVONORGESTREL | | ESTRADIOL | |
|---|---|---|---|
| Micrograms/2.4 sq. cm. | Days | Micrograms/2.4 sq. cm. | Days |
| about 25 | 1 | 6 | 1 |
| 90 | 2 | 10 | 2 |
| 140 | 3 | 16 | 3 |
| 270 | 7 | | |
| 375 | 8 | | |
| 405 | 9 | | |
| 570 | 10 | | |
| 505 | 11 | | |
| 590 | 14 | | |

To obtain maximum flux rates aliquots of the reservoir were analyzed during a period of 8 hours on day 2, day 3, and day 7. The results show zero order release of the hormone from the system on each of the three days at an average rate of 6.7 micrograms per hour (160 micrograms per day/2.4 square/centimeters). Thus a patch with a surface area of 0.5 square centimeters should be capable of delivering 20 micrograms per day of levonorgestrel.

Tests were also conducted with an estradiol-containing patch system with the 2.4 square centimeter estradiol patch, and permeation rates of 5 per day were achieved. At this rate a patch with a surface area of 5 square centimeters would be capable of delivering 2.5 milligrams per day of levonorgestrel.

Table 3 sets forth the properties of a patch-type sustained release system:

TABLE 3

| PROPERTIES OF DERMAPATCH ® SUSTAINED RELEASE SYSTEM | | |
|---|---|---|
| | LEVONORGESTREL | ESTRADIOL |
| SYSTEM CHARACTERISTICS | | |
| Surface area, sq. cm. | 2.4 | 2.4 |
| Loading dose, mg. | 31 | 32.6 |
| MOUSE SKIN PERMEATION | | |
| Rate of permeation mcg./sq. cm./hr. | 0.75-2.8 | >0.09* |
| Minimum dose absorbed, mcg./24 hr. | 43-160 | >5.2 |
| Period permeation studied, days | 14 | 3 |
| ESTIMATED PATCH SIZE REQUIRED | | |
| Dose required, mcg./day | 20 | 25 |
| Estimated size needed to deliver required dose, sq. cm. | 0.5 | 5 |
| Expected duration, days | >7 | >7 |

*These are minimum values which have not been corrected for saturation effects. It is expected that the maximum flux rates will be nearly 2-3 times greater.

LIST OF REFERENCES

Daster, et al., *American Pharmacy*, NS22, 2, 29–35, February 1982.

Feldman, R. J. and Maibach, H. I., *J. Invest. Derm.* 52, 89 (1969).

Schaefer, H., Stuttgen, G. and Schalla, W., Contraception via Topical Application?—A Review—, *Contraception*, 20 (3), 225 (1979).

Scheuplein, R. J. and Blank. I. H., Permeability of the Skin, *Physiol. Rev.*, 51, 702 (1971).

Vickers, C. F. H., *Arch. Dermatol.* 88, 20–25 (1963).

What is claimed is:

1. A transdermal drug delivery system, which system comprises:
   (a) an impervious backing sheet;
   (b) a macroporous, nondrug rate-controlling, liquid-base-retaining face member, which macroporous membrane has pores of sufficiently large size, to avoid rate control of the drug to be transdermally delivered, and of sufficiently small size, to provide a controlled amount of a thin film of a base material to the skin of the user;
   (c) the backing sheet and the macroporous membrane secured together to form an intermediate reservoir therebetween; and
   (d) the reservoir having a composition therein comprising:
      (i) a dermatologically acceptable viscous liquid base material, which liquid base material is selected to exude in a controlled amount through the pores of the face membrane, to form a thin film on the skin of the user and to occlude the skin of the user and to force hydration of the stratum corneum layer with water from the lower layers of the epidermis of the user in use; and
      (ii) a plurality of solid, drug-rate-controlling microparticles generally uniformly dispersed and suspended in the liquid base material in the reservoir in an amount to provide for the desired time period of delivery of the drug to be transdermally delivered, the microparticles having a particle size of less than about 1000 microns and containing an effective therapeutic amount of a drug for transdermal delivery, the active drug material for transdermal delivery and the liquid base material being compatible to form a compatible transport relationship, whereby, on application to the skin of a user of the transdermal drug delivery system, the liquid base material exuded from the macroporous membrane forms a stable thin film on intimate contact with the skin of the user, while the drug is released at a controlled release rate from the suspended microparticles into the liquid base material and directly into the skin of the user.

2. The drug delivery system of claim 1 wherein the macroporous face membrane has a pore size of about 1 to 1000 microns.

3. The drug delivery system of claim 1 wherein the viscous liquid base material comprises a hydrophilic material and the drug to be delivered comprises a water soluble drug.

4. The drug delivery system of claim 1 wherein the liquid base material comprises a hydrophobic viscous material and the drug to be transdermally delivered comprises a hydrophobic drug.

5. The drug delivery system of claim 1 wherein the liquid base material comprises a glycerol water-containing liquid base material and wherein the drug to be transdermally delivered comprises a water soluble drug.

6. The drug delivery system of claim 1 wherein the liquid base material comprises a viscous hydrocarbon-type material and wherein the drug to be transdermally delivered comprises a hydrophobic drug soluble in the viscous hydrocarbon liquid base material.

7. The drug delivery system of claim 1 wherein the active drug comprises a contraceptive steroid hormone.

8. The drug delivery system of claim 7 wherein the contraceptive steroid hormone is selected from the group consisting of norethindrone, norgestrel, estradiol, levonorgestrel, and mestranol and combinations thereof.

9. The drug delivery system of claim 8 wherein the liquid base material comprises a viscous long chain hydrocarbon material.

10. The drug delivery system of claim 1 which includes a removable means to seal the face of the macroporous membrane prior to use; and means to secure the face membrane to the skin of a user.

11. The drug delivery system of claim 1 wherein the microparticle comprises a microparticle having a particle size of about 200 microns or less and wherein the active ingredient comprises a levonorgestrel or estradiol wherein the active drug is admixed with a lactide or glycolide polymer and wherein the microparticle has a wall thickness composed of a lactide or glycolide polymer.

12. The drug delivery system of claim 1 wherein the microparticles comprise a solid admixture of the drug and a biodegradable polymer and a thin outer layer of a biodegradable polymer.

13. A transdermal drug delivery system for the delivery of a contraceptive steroid drug to the skin of a user, which system comprises:
(a) an impervious backing sheet;
(b) a macroporous face membrane having a pore size of from about 1 to 1000 microns, the pores of sufficient size to avoid rate control of the contraceptive hormone to be transdermally delivered by the drug delivery system;
(c) the backing sheet and the macroporous membrane sheet secured together to form an intermediate reservoir therebetween;
(d) means to seal the face of the macroporous face membrane prior to use, said means being easily removable by the user prior to use;
(e) adhesive securing means to permit the macroporous face membrane to be placed in contact with the skin of the user after removal of the protective means; and
(f) the reservoir having a composition therein comprising:
 (i) a dermatologically acceptable hydrophobic viscous hydrocarbon liquid base material to occlude the skin of the user and force hydration of the stratum corneum layer with water from the lower layers of the epidermis of the user; and
 (ii) a plurality of drug-rate-controlling solid microparticles having a particle size of less than about 300 microns, the microparticles generally uniformly dispersed and suspended in the liquid base material in an amount of about 5 to 70 weight percent of the composition, and having a wall coating of about 0.1 to 20 microns and adapted and designed to provide for zero order release, the microparticles containing an effective therapeutic amount of a contraceptive steroid drug for transdermal delivery to the user, the steroid characterized by having a low water solubility and being generally hydrophobic, whereby, on application to the skin of a user of the liquid drug delivery system, the liquid base material exuded from the macroporous face membrane forms a stable thin film in intimate contact with the skin of the user, while the steroid hormone is released from the solid microparticles in a desired rate pattern through the liquid base material and directly transdermally into the skin of the user.

14. The drug delivery system of claim 1 wherein the amount of the drug in the microparticles varies from about 0.1 to 30 weight percent of the microparticles.

15. The drug delivery system of claim 1 wherein the viscous liquid base material comprises a jelly-like hydrocarbon having a melting point of about 38° C. to 60° C.

16. The drug delivery system of claim 1 wherein the amount of microparticles dispersed in the liquid base material comprises from about 5 to 70 weight percent of the composition.

17. The drug delivery system of claim 1 wherein the drug comprises a contraceptive steroid to be transdermally delivered at a rate of about 5 to 150 micrograms per day.

18. The drug delivery system of claim 1 wherein the microparticles provide a zero-order release pattern to the transdermal delivery of the drug.

* * * * *